United States Patent
Van Dorpe et al.

(10) Patent No.: US 9,150,413 B2
(45) Date of Patent: Oct. 6, 2015

(54) WAVEGUIDE-INTEGRATED PLASMONIC RESONATOR FOR INTEGRATED SERS MEASUREMENTS

(75) Inventors: Pol Van Dorpe, Spalbeek (BE); Pieter Neutens, Sint-Andries (BE)

(73) Assignees: IMEC, Leuven (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 287 days.

(21) Appl. No.: 13/471,254

(22) Filed: May 14, 2012

(65) Prior Publication Data
US 2012/0287429 A1 Nov. 15, 2012

Related U.S. Application Data

(60) Provisional application No. 61/485,682, filed on May 13, 2011.

(51) Int. Cl.
| | |
|---|---|
| *G01J 3/44* | (2006.01) |
| *B82Y 10/00* | (2011.01) |
| *B82Y 20/00* | (2011.01) |
| *G02B 6/122* | (2006.01) |
| *G01N 21/65* | (2006.01) |

(52) U.S. Cl.
CPC ............ *B82Y 10/00* (2013.01); *B82Y 20/00* (2013.01); *G02B 6/1226* (2013.01); *G01N 21/658* (2013.01)

(58) Field of Classification Search
CPC ............ G01J 3/02; G01J 3/44; G01N 21/65; G01N 21/658; G01N 2021/656
USPC ...................... 356/72–73, 300–445
See application file for complete search history.

(56) References Cited

U.S. PATENT DOCUMENTS

2010/0002979 A1* 1/2010 Diest et al. .................. 385/8

OTHER PUBLICATIONS

Chen et al., Focusing plasmons in nanoslits for surface-enhanced Raman scattering, Small, 5(24), 2876-2882, (2009).
Dionne et al.. Plasmon slot waveguides: Towards chip-scale propagation with subwavelengthscale localization, Phys. Rev. B, 73, 035407, (2006).
Ditlbacher et al., Organic diodes as monolithically integrated surface plasmon polariton detectors, Apl. Phys. Lett., 89, 161101, (2006).
Gan et al., Spectrally selective splitters with metal-dielectric-metal surface plasmon waveguides, Appl. Phys. 8, 95, 807-812, (2009).
Han et al., Surface plasmon Bragg gratings formed in metal-insulator-metal waveguides, IEEE Phot. Tech. Lett., 19, 91-93, (2007).
Hosseini et al., A low-loss metal-insulator-metal plasmonic Bragg reflector, Opt. Exp., 14, 11318-11323, (2006).
Liu et al., A wide bandgap plasmonic Bragg reflector. Opt. Exp., 16, 4888-4894, (2008).

(Continued)

*Primary Examiner* — Abdullahi Nur
(74) *Attorney, Agent, or Firm* — McDonnell Boehnen Hulbert & Berghoff LLP (57) ABSTRACT

A resonator structure is disclosed. In some embodiments, the resonator structure may include a metal-insulator-metal waveguide comprising a first metal layer, a second metal layer, and an insulating layer between the first metal layer and the second metal layer, wherein the insulating layer comprises a resonating cavity. The resonator structure may further include a mirror formed in the resonating cavity, wherein the mirror comprises at least one nanoscale metallic reflector positioned at least partly in the insulating layer.

16 Claims, 4 Drawing Sheets

(56) References Cited

OTHER PUBLICATIONS

Liu et al., Characteristics of plasmonic Bragg reflectors with insulator width modulated in sawtooth profiles, Opt. Exp., 18, 11589-11598, (2010).

Matsuzaki et al., Characteristics of gap plasmon waveguide with stub structures, Optics Express, 16(21), 16314-16325, (2008).

Neutens et al., Electrical detection of confined gap plasmons in metal-insultor-metal waveguides, Nat. Phot., 3, 283-286, (2009).

Neutens et al., Electrical Excitation of Confined Surface Plasmon Polaritons in Metallic Slot Waveguides, Nano Let., 10, 1429-1432, (2010).

Walters et al., A silicon-based electrical source of surface plasmon polaritons, Nat. Mat., 9, 21-25, (2010).

Wang et al., Plasmon Bragg reflectors and nanocavities on flat metallic surfaces, Appl. Phys. Lett. 87, 013107, (2005).

* cited by examiner

WAVEGUIDE-INTEGRATED PLASMONIC RESONATOR FOR INTEGRATED SERS MEASUREMENTS

CROSS-REFERENCE TO RELATED APPLICATION

This application claims priority to U.S. Provisional Patent Application No. 61/485,682 filed May 13, 2011, the contents of which are hereby incorporated by reference.

BACKGROUND

Waveguide-integrated passive components may be used to modify the transmission spectrum through a waveguide, such as a metallic slot waveguide. For instance, high Q-factor band-pass filters can be useful to filter a transmitted signal into different spectral bands in order to realize wavelength division multiplexing. Additionally, passive filters can be applied for routing surface plasmon polaritrons (SPPs) through a circuit of waveguides. Passive filters can play an important role for sensing applications too. For example, sharp plasmonic notch filters are useful for a future development of a surface-enhanced Raman scattering setup on chip.

Resonators can be made in a metal-insulator-metal (MIM) plasmonic waveguide that show strong resonance. In order to obtain such a strong resonance, Bragg reflectors or Bragg mirrors are typically used. The resonators are made by introducing a resonant cavity in a Bragg reflector inside a MIM plasmonic waveguide. Bragg reflectors based on MIM waveguides have been demonstrated experimentally recently.

The modulation is achieved by varying the dielectric thickness and may be studied numerically. Physically, in these waveguides the alternative variation in the thickness leads to periodic modulation of the mode index. For example, for a 100 nm thick $SiO_2$ core symmetrically surrounded by two semi-infinite gold cladding layers, the mode index equals 1.84 at a free space wavelength of 800 nm. When the core thickness is decreased to 60 nm, the mode index rises to 2.06. This modal index difference is the key point to designing these Bragg reflectors inside MIM waveguides.

When a cavity is introduced within the Bragg reflector, a sharp resonance appears in the stop-band of the Bragg reflector. In silicon photonics, photonic bandgap microcavities are known to have a resonance with a very high quality-factor approaching, for example, up to $10^8$. However, if one transfers this concept from a very low-loss dielectric waveguide to a high-confinement metallic waveguide, losses increase dramatically due to the field penetration inside the metal layers, causing high ohmic losses. Combined with previously developed active plasmonic components, sharp plasmonic band-pass filters and notch filters inside metallic waveguides can lead to microscale fluorescence biosensors or integrated detection of surface enhanced Raman scattering. The passive filters are integrated in MIM waveguides due to the good field confinement.

SUMMARY

When using surface plasmon polaritrons (SPPs), the use of Bragg reflectors may have some disadvantages due to the relatively long length of micron-sized Bragg reflectors, resulting in the need for a long propagation length of confined SPPs.

Disclosed are optical resonators, including waveguide-integrated plasmonic resonators, with a high quality factor and nanoscale size dimensions. With the disclosed optical resonators, SPPs may be integrated with a surface enhanced Raman scattering (SERS) setup.

In the disclosed optical resonators, the travelling length that highly-confined SPPs need to travel can be short, which may be advantageous in view of the typical short propagation length of polaritons. In some embodiments, nanometer scale reflectors can be used, resulting in miniaturized travelling lengths for SPPs in the optical resonator.

In some embodiments, a completely integrated SERS setup can be created on-chip using, for example, a waveguide-integrated plasmonic resonator.

In some embodiments, the disclosed optical resonators may very efficiently couple Raman scattered photons to the SPPs in the optical resonator, as well as to the output waveguide when in resonance conditions. Once captured by the output-waveguide, the Raman scattered plasmons can, for example, be spectrally analyzed by either out-coupling the plasmons to free-space radiation and subsequent spectral analysis, or by using integrated dispersive optics. Based on the above, the problem of non-radiatively decay which could occur if Raman scattered photons are coupled to plasmonic excitations is less of a problem.

In one aspect, a resonator structure is disclosed. In some embodiments, the resonator structure may include a metal-insulator-metal waveguide comprising a first metal layer, a second metal layer, and an insulating layer between the first metal layer and the second metal layer, wherein the insulating layer comprises a resonating cavity. The resonator structure may further include a mirror formed in the resonating cavity, wherein the mirror comprises at least one nanoscale metallic reflector positioned at least partly in the insulating layer.

In another aspect, a surface-enhanced Raman scattering (SERS) system is disclosed that includes a surface resonator, such as the surface resonator described above.

In yet another aspect, a method is disclosed that includes providing a SERS system, such as the SERS system described above, and using the SERS system to perform SER spectrometry.

Particular aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

The drawings are only schematic and are non-limiting. In the drawings, the size of some of the elements may be exaggerated and not drawn on scale for illustrative purposes. Any reference signs in the claims shall not be construed as limiting the scope. In the different drawings, the same reference signs refer to the same or analogous elements.

DETAILED DESCRIPTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In the following description, nanoscale may be understood to refer to an object having at least one dimension being smaller than the plasmon wavelength. In some embodiments, nanoscale may be understood to refer to an object having at least one dimension in at least one direction being between 1000 nm and 1 nm, between 100 nm and 1 nm, or even between 50 nm and 1 nm.

Further, in the following description, to a metal-insulator-metal (MIM) waveguide may be understood as a waveguide formed by two metal layers (M) and an insulator layer (I) sandwiched in between the two metal layers.

Still further, in the following description, a resonating structure may be understood as a structure comprising at least one resonating cavity, wherein radiation with particular properties can resonate. The latter may result in a structure having a particular filtering or radiation enhancing effect.

Yet further, in the following description, a high index contrast dielectric waveguide may be understood as a waveguide made in any type of system providing a high index contrast, such as, for example, a silicon-on-insulator (SOI) material system or a III-V material system. In some embodiments, a SOI material system may be used in order to allow for highly integrated photonic circuits. The high refractive index contrast allows photonic waveguides and waveguide components with submicron dimensions to guide, bend, and control light on a very small scale so that various functions can be integrated on a chip. Using a SOI material system may also have some technological advantages. Due to the complementary metal-oxide-semiconductor (CMOS) industry, silicon technology has reached a level of maturity that outperforms any other plane chip manufacturing technique by several orders of magnitude in terms of performance, reproducibility, and throughput. Nano-photonic integrated circuits can be fabricated with wafer scale-processes, which means that a wafer can contain a large number of photonic integrated circuits. Combined with the commercial availability of large wafers at a relative moderate cost, this means that the price per photonic integrated circuit can be very low.

Disclosed herein is a resonator structure for supporting radiation in a resonating cavity. The resonator structure comprises a metal-insulator-metal (MIM) waveguide. Such a MIM waveguide typically comprises two metal layers and an insulating layer sandwiched between the two metal layers. The resonator structure also comprises at least one nano-scale metallic reflector. The at least one nano-scale metallic reflector may be positioned at least partly in the insulating layer and may form at least one mirror of a resonating cavity of the MIM waveguide, where the resonating cavity is positioned in the insulating layer.

Figure 1A:
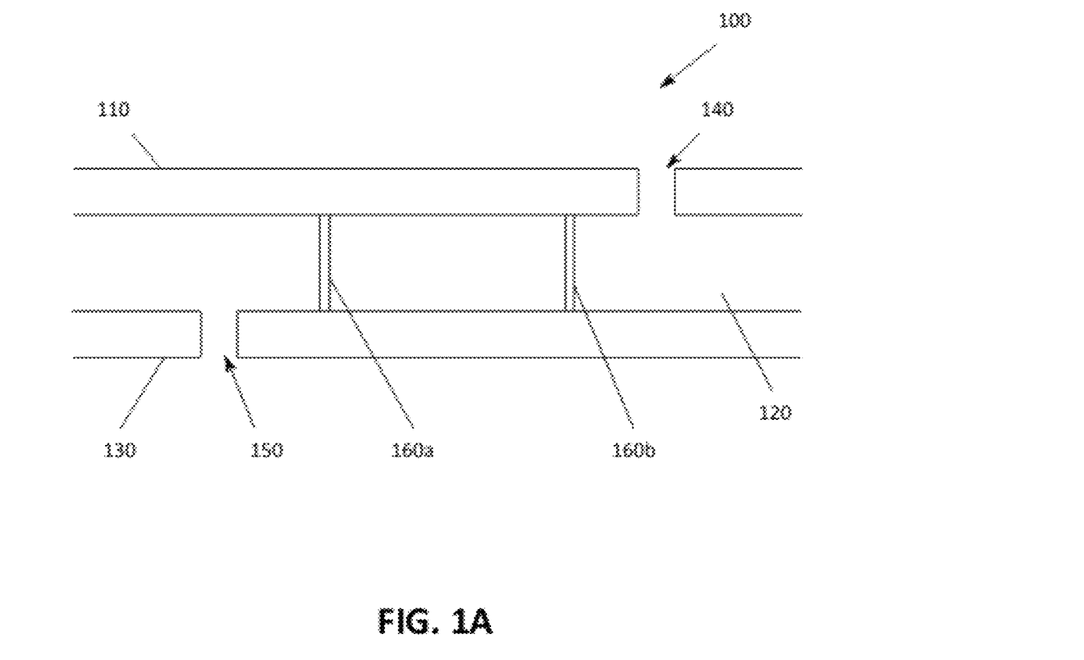
FIG. 1A illustrates a schematic overview of a metallic reflector resonator filter, in accordance with some embodiments.

By way of illustration, a more detailed description of features and advantages of resonating structures according to at least some embodiments of the present invention is given with reference to the exemplary resonating structure shown in FIG. 1A, embodiments of the present invention not being limited thereto. In FIG. 1A, a schematic representation of a possible implementation of the high quality factor optical resonator of an embodiment of the present invention is given. FIG. 1A shows a resonating structure 100 comprising a MIM waveguide, which comprises two metal layers 110, 130 and an insulating layer 120 sandwiched therein between. In some embodiments, a gold-SiO$_2$-gold MIM waveguide may be used with an insulator core thickness of around 100 nm. Other materials and dimensions are possible as well.

As shown, the resonating structure 100 also comprises a radiation inlet 140 for guiding radiation into the structure and a radiation outlet 150 for guiding radiation out of the waveguide. The resonating structure furthermore comprises a cavity structure formed by at least one, in the present example being two, metal reflectors 160a, 160b. The metal reflectors 160a, 160b may comprise, for example, vertical gold barriers with a thickness of, for example, between 0 nm and 60 nm. Due to partial optical transmission and reflection occurring at the two thin gold barriers, a resonance may be formed according to equation [1]:

$$2L_{cav}k_{SPP}+2\Phi=2n\pi \quad [1]$$

where $L_{cav}$ is the cavity length, $k_{SPP}$ is the SPP wave vector, $\Phi$ is a phase shift upon reflection, and n is an integer number.

Thus, as shown in FIG. 1A, a high quality resonating structure may be achieved by incorporating metallic reflectors inside the MIM waveguide. In particular, a waveguide-integrated transmission filter based on an integrated Fabry-Perot resonator with nanoscale size in three dimensions can be designed by introducing two thin metallic barriers in a MIM waveguide. In this way it is possible to remove the necessity of micron-size Bragg gratings, making it possible to create a resonator on nano-scale in three dimensions. Due to its small dimensions, losses due to resistive heating may also be strongly reduced, leading to a higher overall transmitted power at resonance.

When operating the disclosed high quality factor resonator in off-resonance wavelengths, no efficient resonant coupling to the cavity is possible and, as a consequence, the transmission will be very low since the two metal barriers are highly reflective. This is a great advantage compared to the cavities based on Bragg gratings, since the transmission for off-resonant wavelengths is very low over the entire spectrum, while for plasmonic crystal cavities the spectral range of the zero-transmission region only has a limited spectral range determined by the stop-band of the Bragg gratings.

In order to study the spectral transmission through the cavity filter of the disclosed high quality factor resonator, two-dimensional finite-difference time-domain (FDTD) simulations were performed. SPP generation inside the waveguide was achieved by dipole excitation, and the transmitted power after the filter was monitored.

In order to get an absolute value for the transmission through the filter, it was necessary to account for the SPP decay inside the waveguide. To this end, the power spectrum after the filter was normalized to the power spectrum for the case where no filter is present.

Figure 1B:
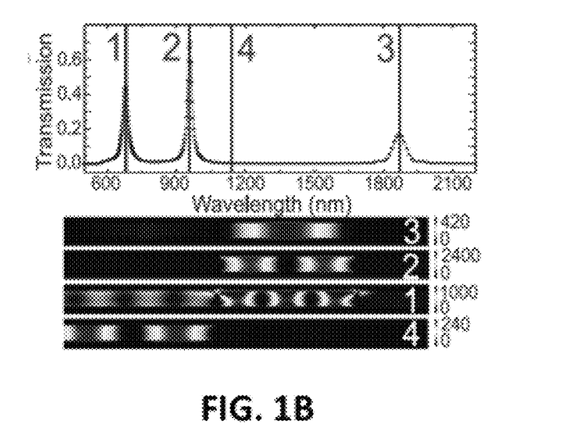
FIG. 1B illustrates normalized transmitted power for a 500 nm long cavity together with the normalized electric field profiles for a high quality factor optical resonator, in accordance with some embodiments.

The normalized transmission spectrum of a 500 nm wide cavity with 20 nm wide metal reflectors is shown in FIG. 1B. For this width, it is observed that the three first resonant modes (n=1, 2, 3) fit in the cavity for free space wavelengths between 500 and 2200 nm. In the bottom panel of FIG. 1B, the normalized electric field profile inside the cavity is shown for the different wavelengths indicated by the arrows in the transmission spectrum. For the resonant wavelengths (lines 1, 2 and 3), nodes are found inside the cavity and SPP transmission is observed after the cavity. In the fourth normalized E-field profile, corresponding with line 4 in the transmission spectrum, the normalized electric field profile for an off-resonant wavelength of 1.15 μm is shown. No SPP transmission is observed in this case, as only a strong reflection is observed at the first and second gold barrier.

Figure 2:
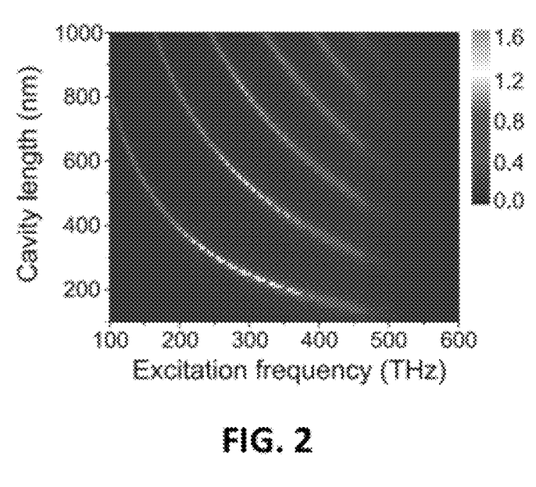
FIG. 2 illustrates a plot of transmitted power through the cavity filter of the high quality factor optical resonator as a function of the excitation frequency and the cavity length, in accordance with some embodiments.

The method of tuning the center wavelength of the resonance is determined by the previously defined resonance condition. As is the case for plasmonic crystal resonators and many other resonators, the spectral position of the resonance can be altered by changing the cavity length. FIG. 2A depicts a plot of the transmitted power through the filter as a function of the excitation frequency and the cavity length. A standard Fabry-Perot mode plot may be obtained. The spectral region where interband transitions lead to increased losses in the cladding layers can clearly be seen at the right of the plot. The lowest order mode (n=1) appears for a cavity length of 150 nm.

For increasing cavity lengths, higher order resonant modes appear in the spectral transmission. The predicted spectral shift as a function of the cavity length is clearly observed. A sharp resonance that is indicative of a high quality-factor mode is observable for all nanocavities. The quality factor for the nanocavity resonances is mainly determined by the intrinsic metallic losses from both the waveguide cladding layers and the metallic mirrors.

In order to investigate the quality factor, it is possible to study the effect of changing the efficiency of the two gold barrier reflectors on the quality factor. The reflectivity from and transmission through the gold barriers can easily be changed by altering their thickness. With an increase in barrier thickness and hence an increasing reflector efficiency, a stronger resonance is obtained and, as a result, a narrowing of the spectral width is observed. The resulting Q-factors for the n=1, 2 and 3 is plotted in FIG. 3A as a function of the barrier thickness. The width of the cavities is taken to be respectively 250, 500 and 700 nm in order to have the resonant wavelength for the three modes around a value of 1000 nm. The quality factor is found to be an increasing function of the barrier thickness. However, if the barrier thickness becomes too large, the reflection becomes too large to efficiently couple in from the propagating plasmon mode to the resonant cavity. Therefore, above a thickness of 40 nm, the quality factor saturates and eventually decreases. Of course this effect manifests itself in the transmitted power through the filter, which is depicted in FIG. 3B, again for the three lowest modes. As the reflector thickness increases, the Q-factor increases but due to a lower incoupling efficiency, the transmission through the filter decreases. Above 40 nm, almost no power is transmitted through the resonant cavity.

Although the simulations presented above are two-dimensional FDTD simulations, three-dimensional simulations prove that this type of resonator can also be applied in waveguides with sub-wavelength lateral dimensions.

In some embodiments, the resonating system also may comprise dispersive optics. Such dispersive optics may be integrated dispersive optics that can be implemented in the plasmonic waveguides themselves by integrating additional filters, or may allow efficiently coupling the surface plasmons to low-loss high index contrast dielectric waveguides fabricated from, for example, SiN, silicon, GaN, or other materials. In these dielectric waveguides, integrated spectral analysis can be performed using, for example, photonic crystals or arrayed waveguide gratings. Combining this with integrated detectors and integrated laser sources, this can give rise to completely integrated SERS sensors.

Also disclosed is a SERS system, such as a SERS sensor, that includes a resonator structure (100), such as that shown in FIG. 1A. When the thickness of the MIM insulator layer is sufficiently small, very high field enhancements can be obtained inside the high quality resonant cavity. Nanoslit resonant cavities can be used for SERS, due to the high field enhancement inside the slit. The strength of the resonances can be tuned by altering the metallic reflector thicknesses, leading to quality factors up to 100.

In some embodiments, the required Raman system (which is a bulky system including laser sources, spectrometers, and charge-coupled device (CCD) cameras) is integrated on-chip. The disclosed integrated resonator may be suitable to fabricate a completely integrated SERS device where molecules are introduced inside the resonant cavity and the Raman scattered plasmons are efficiently conducted outside the cavity. The Raman scattered plasmons can be guided and used for spectral analysis of the Raman scattered signal. To completely integrate the system on chip, it can be combined with active plasmon sources and detectors.

Among other advantages, the disclosed resonator may be completely integrated on-chip, may have nano-scale dimensions, may be produced in large arrays for multiplexing, and may have a high Q-factor resonance leading to a high field enhancement, and thus a large SERS intensity.

Figure 4:
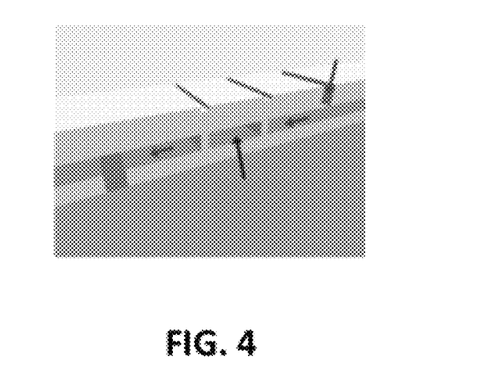
FIG. 4 shows a schematic picture of a metallic reflector resonator filter, in accordance with some embodiments.

Also disclosed is a method for using a resonating structure or an SERS system, such as those disclosed above. For purposes of illustration, a numerical example is shown of how a waveguide-integrated cavity structure may be realized by incorporating metallic reflectors inside the waveguide. In this way, the necessity of micron-size Bragg gratings can be removed, resulting in an advantageous resonator on nanoscale in three dimensions. Due to its small dimensions, losses due to resistive heating may be strongly reduced, leading to a higher transmitted power at resonance. In FIG. 4, a schematic representation of the structure under study is given. A standard gold-SiO2-gold MIM waveguide was used with an insulator core thickness of 100 nm. The cavity structure was formed by two vertical gold barriers. In practice, this structure could be fabricated by focused ion beam milling inside the insulator layer, followed by gold evaporation or electroplating of the top metal layer. Due to partial optical transmission and reflection occurring at the two thin gold barriers, a resonance is formed when Equation [1] is satisfied.

For off-resonance wavelengths, no efficient resonant coupling to the cavity is possible and as a consequence the transmission will be very low since the two metal barriers are highly reflective. This may be an advantage compared to the plasmonic crystal cavities, since the transmission for off-resonant wavelengths is very low over the entire spectrum, while for plasmonic crystal cavities the spectral range of the zero-transmission region only has a limited spectral range determined by the stop-band of the Bragg gratings.

In order to study the spectral transmission through the cavity filter, two-dimensional FDTD simulations were performed. SPP generation inside the waveguide was achieved by dipole excitation. The transmitted power after the filter was monitored. In order to get an absolute value for the transmission through the filter, the SPP decay inside the waveguide was accounted for. In particular, the power spectrum after the filter was normalized to the power spectrum for the case where no filter is present.

Figure 5:
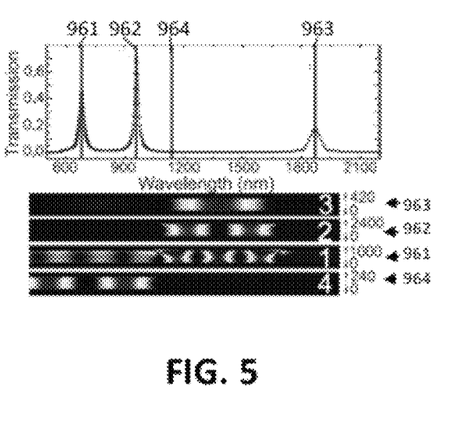
FIG. 5 shows the normalized transmitted power for a 500 nm long cavity together with the normalized electric field profiles, in accordance with some embodiments.

The normalized transmission spectrum of a 500 nm wide cavity with 20 nm wide metal reflectors is shown in the top panel of FIG. 5. For this width, it was observed that the three first resonant modes (n=1, 2, 3) fit in the cavity for free space wavelengths between 500 and 2200 nm. In the bottom panel of FIG. 5, the normalized electric field profile inside the cavity is shown for the different wavelengths indicated by the vertical lines in the transmission spectrum. For the resonant wavelengths (line 961, 962 and 963), clearly 1, 2 and 3 nodes were found inside the cavity, and SPP transmission was observed after the cavity. In the fourth normalized E-field profile, corresponding with line 964 in the transmission spectrum, the normalized electric field profile for an off-resonant wavelength of 1.15 µm was shown. No SPP transmission was observed in this case as only a strong reflection was observed at the first and second gold barrier.

The principles of tuning the resonant wavelength of the integrated metallic reflector resonator can be similar to the tuning of a plasmonic crystal waveguide resonator. The spectral position of the resonance can be altered by changing the cavity length. FIG. 2 depicts a plot of the transmitted power through the filter as a function of the excitation frequency and the cavity length. A standard Fabry-Perot mode plot was obtained. The spectral region where interband transitions led to increased losses in the cladding layers can clearly be seen at the right of the plot. The lowest order mode (n=1) appears for a cavity length of 150 nm. For increasing cavity lengths, higher order resonant modes appear in the spectral transmission. The predicted spectral shift as a function of the cavity length was clearly observed. A sharp resonance that is indicative of a high quality-factor mode was observable for all nanocavities. The quality factor for the nanocavity resonances was mainly determined by the intrinsic metallic losses from both the waveguide cladding layers and the metallic mirrors. From the plot, it can already be noticed that for the same excitation frequency, the quality factor for the second order mode is higher than the first order mode.

Figure 6:
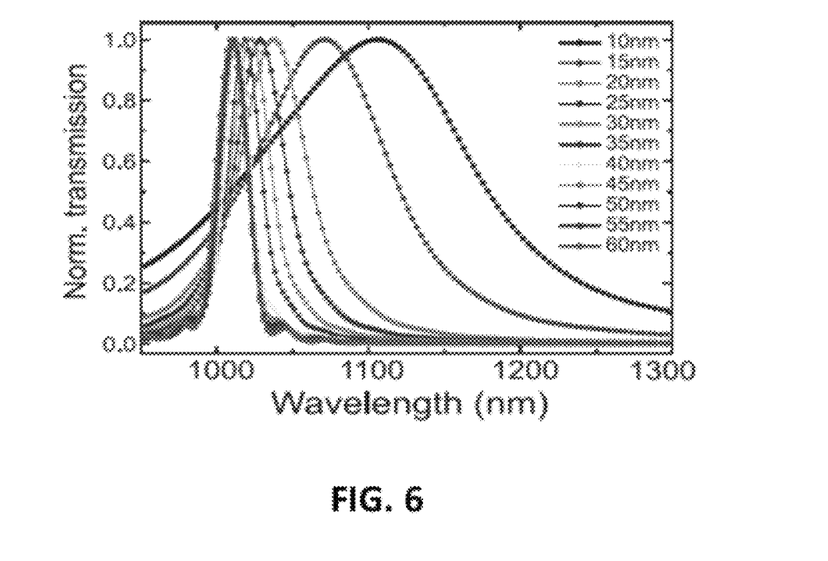
FIG. 6 shows the transmitted power normalized to the peak value as a function of the gold barrier thickness, in accordance with some embodiments.

In order to investigate the quality factor, the effect of changing the efficiency of the two gold barrier reflectors on the quality factor was studied. The reflectivity from and transmission through the gold barriers can easily be changed by altering their thickness. In FIG. 6, the transmission through a 250 nm long cavity resonator is calculated for the first order mode. The thickness of the gold barrier reflectors was varied from 10 to 60 nm. Since the transmitted power through the resonator varied over several orders of magnitude for the different reflector widths, the transmission spectrum was normalized to the peak value. With an increase in barrier thickness and hence an increasing reflector efficiency, a stronger resonance was obtained and as a result a narrowing of the spectral width was observed.

Figure 3A:
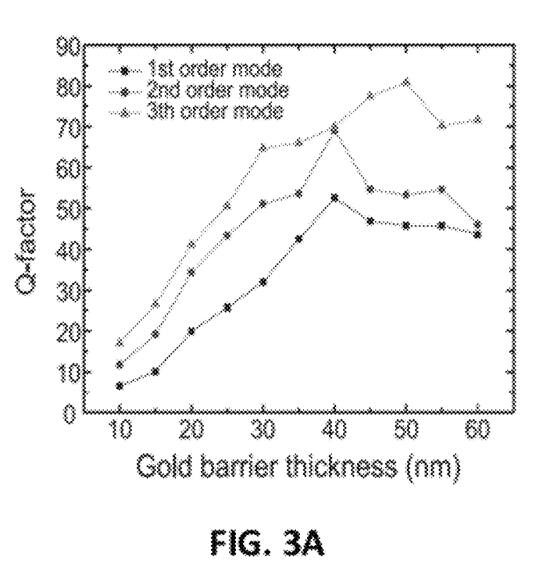
FIG. 3A illustrates the resulting Q-factors as a function of the barrier thickness of the gold barrier reflectors in the high quality factor optical resonator, in accordance with some embodiments.

The resulting Q-factors for the n=1, 2 and 3 were plotted in FIG. 3A as a function of the barrier thickness. The width of the cavities is taken to be respectively 250, 500 and 700 nm in order to have the resonant wavelength for the three modes around a value of 1000 nm. The quality factor was found to be an increasing function of the barrier thickness. However, it was also found that if the barrier thickness became too large, the reflection became too large to efficiently couple in from the propagating plasmon mode to the resonant cavity. Therefore, above a thickness of 40 nm, the quality factor saturates and eventually decreases. Of course, this effect manifests itself in the transmitted power through the filter, which is depicted in FIG. 3B, again for the three lowest modes. As the reflector thickness increases, the Q-factor increases but due to a lower incoupling efficiency, the transmission through the filter decreases.

Figure 3B:
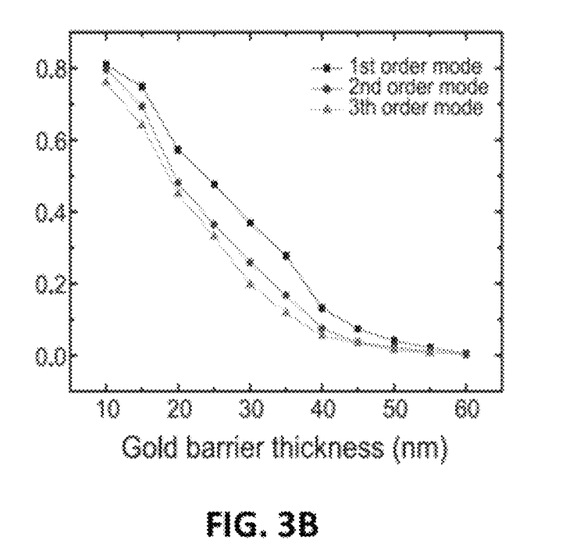
FIG. 3B illustrates the resulting Q-factor in the high quality factor optical resonator when the barrier thickness becomes too large, in accordance with some embodiments.

Above 40 nm, almost no power is transmitted through the resonant cavity. Although the simulations presented in this example are two-dimensional FDTD simulations, three-dimensional simulations prove that this type of resonator can also be applied in waveguides with subwavelength lateral dimensions.

In conclusion, a waveguide-integrated transmission filter based on an integrated Fabry-Perot resonator with nanoscale size in three dimensions could be designed by introducing two gold barriers in a MIM waveguide. The strength of the resonances could be tuned by altering the metallic reflector thicknesses, leading to quality factors up to 80. The disclosed metallic reflector resonators can be used as a waveguide-integrated resonator with nanoscale size in three dimensions. Alternatively or additionally, this type of high quality resonators may be integrated inside nanoscale metallic waveguides with subwavelength lateral dimensions. By modal coupling to such resonators, a novel efficient notch filter can be designed.

The invention claimed is:

1. A surface-enhanced Raman scattering (SERS) system comprising:
   a high index contrast dielectric waveguide; and
   a resonator structure for supporting radiation in a resonating cavity, the resonator structure comprising:
      a metal-insulator-metal (MIM) waveguide comprising a first metal layer, a second metal layer, and an insulating layer between the first metal layer and the second metal layer,
      at least two nanoscale metallic reflectors positioned at least partly in the insulating layer and forming at least two mirrors of the resonating cavity in the insulating layer, and
      integrated dispersive optics for coupling surface plasmons from the resonator structure to the high index contrast dielectric waveguide.

2. The SERS system of claim 1, further comprising one or both of an integrated detector and an integrated radiation source.

3. The SERS system of claim 1, wherein the system comprises a lab-on-chip system.

4. The SERS system of claim 1, wherein the at least two nanoscale metallic reflectors comprise at least two barriers substantially perpendicular to the first metal layer and the second metal layer.

5. The SERS system of claim 4, wherein the at least two barriers comprise gold barriers.

6. The SERS system of claim 4, wherein the thickness of the at least two barriers is between about 1 nm and 100 nm.

7. The SERS system of claim 6, wherein the thickness of the at least two barriers is between about 1 nm and about 40 nm.

8. The SERS system of claim 1, wherein the resonator structure further includes a radiation inlet configured to couple radiation into the resonator structure, and a radiation outlet configured to couple radiation out of the resonator structure.

9. A method comprising:
   providing a surface-enhanced Raman scattering (SERS) system comprising:
      a high index contrast dielectric waveguide, and
      a resonator structure for supporting radiation in a resonating cavity, the resonator structure comprising:
         a metal-insulator-metal (MIM) waveguide comprising a first metal layer, a second metal layer, and an insulating layer between the first metal layer and the second metal layer,
         at least two nanoscale metallic reflectors positioned at least partly in the insulating layer and forming at least two mirrors of the resonating cavity in the insulating layer, and
         integrated dispersive optics for coupling surface plasmons from the resonator structure to the high index contrast dielectric waveguide; and
   using the SERS system to perform surface-enhanced Raman spectrometry.

10. The method of claim 9, wherein the at least two nanoscale metallic reflectors comprise at least two barriers substantially perpendicular to the first metal layer and the second metal layer.

11. The method of claim 10, wherein the at least two barriers comprise gold barriers.

12. The method of claim 10, wherein the thickness of the at least two barriers is between about 1 nm and 100 nm.

13. The method of claim 12, wherein the thickness of the at least two barriers is between about 1 nm and about 40 nm.

14. The method of claim 9, wherein the resonator structure further includes a radiation inlet configured to couple radiation into the resonator structure, and a radiation outlet configured to couple radiation out of the resonator structure.

15. The method of claim 9, wherein the SERS system further comprises one or both of an integrated detector and an integrated radiation source.

16. The method of claim 9, wherein the SERS system comprises a lab-on-chip system.

* * * * *